(12) United States Patent
Novak

(10) Patent No.: US 6,824,539 B2
(45) Date of Patent: Nov. 30, 2004

(54) TOUCHSCREEN CONTROLLING MEDICAL EQUIPMENT FROM MULTIPLE MANUFACTURERS

(75) Inventor: Pavel Novak, Schaffhausen (CH)

(73) Assignee: Storz Endoskop Produktions GmbH (DE)

( * ) Notice: Subject to any disclaimer, the term of this patent is extended or adjusted under 35 U.S.C. 154(b) by 168 days.

(21) Appl. No.: 10/211,653

(22) Filed: Aug. 2, 2002

(65) Prior Publication Data
US 2004/0024384 A1 Feb. 5, 2004

(51) Int. Cl.[7] ............................................... A61B 17/00
(52) U.S. Cl. ........................................... 606/1; 600/101
(58) Field of Search ..................... 606/1, 4, 65; 600/34, 600/41, 301, 101; 604/65

(56) References Cited

U.S. PATENT DOCUMENTS

| | | | |
|---|---|---|---|
| 5,788,688 A | 8/1998 | Bauer et al. | |
| 6,117,126 A | * 9/2000 | Appelbaum et al. | ............ 606/1 |
| 6,397,286 B1 | 5/2002 | Chatenever et al. | |
| 6,432,065 B1 | * 8/2002 | Burdorff et al. | ............ 600/566 |
| 2002/0147455 A1 | * 10/2002 | Carson | ........................ 606/130 |

OTHER PUBLICATIONS

Karl Storz Endoskip GmbH, Specification, Jan. 1995.

Endoworld, A Karl Storz GmbH communication, Nov. 1999.

* cited by examiner

Primary Examiner—Beverly M. Flanagan
(74) Attorney, Agent, or Firm—St. Onge Steward Johnston & Reens LLC

(57) ABSTRACT

A communication system including a bus, interconnecting first and third party surgical devices, and a touchscreen, operated with the bus and displaying replicas control interfaces of the first and third party surgical devices, and facilitating remote control of the first and third party surgical devices during a surgical procedure.

37 Claims, 10 Drawing Sheets

| ST | Diagram | Nomenclature | Faceplate |
|---|---|---|---|
| | | Arthroscopic<br>Gastroenterology<br>Gynecology<br>Laparoscopy | |

Figure 5A

| Manufacturer | Power Supply | Laser Elec. Control | Gas Insufflator |
|---|---|---|---|
| KS | X | | X |
| 3rd$_1$ | X | X | X |
| 3rd$_2$ | | X | X |

TOUCHSCREEN CONTROLLING MEDICAL EQUIPMENT FROM MULTIPLE MANUFACTURERS

FIELD OF THE INVENTION

A communication system for connecting and controlling various devices through a screen that displays replicas of the various devices' control interfaces to facilitate remote control of these various devices.

BACKGROUND OF THE INVENTION

Systems have been developed to augment a human surgeon's ability to perform surgery on a patient by providing the surgeon with an intra-operative image of anatomical structures within the patient's body. Typically, these systems comprise a specialized form of camera or medical endoscope. Further, a class of these systems, which includes endoscopic and laparoscopic instruments, has reduced the invasive nature of many surgical procedures.

This class of systems has two salient characteristics in common: First, the surgeon using the system cannot directly manipulate the patient's anatomy with his fingers, and second, the surgeon cannot directly observe what he is doing. Instead, the surgeon must rely on a variety of instruments that can be inserted through a trocar or through a working channel of an endoscope and is controlled from a remote location. Often the surgeon must rely on an assistant to adjust parameters of the endoscopic instruments that typically are located outside the sterile environment of the operating station.

U.S. Pat. No. 6,397,286 to Chatenever et al. ("the '286 patent") discloses a system for increasing the surgeon's control over numerous instruments, a bus connecting the instruments utilized in a surgical procedure has been utilized. Conceptually, the bus allows numerous devices having different network mastering and slave capabilities to communicate with one another in response to the signals generated by the surgeon during the procedure.

Furthermore, in a modular communication system for central and sterile operation of medical devices, such as a variety of instruments used in an endoscopic operation, each of them may be used in a time-limited manner that necessitates frequent connection of these instruments to a network. In addition, each of the medical devices within the network has to be controlled during an operation. Accordingly, it is imperative that these operations be conducted in a seamless manner without interrupting an on-going operation. As disclosed in a patent application Ser. No. 09/411,412 filed on Oct. 1, 1999 and entitled "Bus Extension For Multiple Masters," such seamless control over all stages of the endoscopic operation becomes particularly important when the network extends across a wide area. Both of the above mentioned applications are owned by the same Assignee as this application and are incorporated herein by reference.

The above disclosed communication systems provide reliable coordination between various instruments. A network master is capable of identifying and communicating with each device utilized in endoscopic operations as long as both master and slave devices use the same system management protocol.

Typically, the surgeon has to communicate instructions to a staff of assistants if either surgery configuration, or existing parameters need to be modified. In other words, if the surgeon needs to use a device that has not been connected to the bus or to change a parameter of an already engaged device, an assistant must be instructed to manipulate the master device or control interface of a control unit of the slave device to meet the surgeon's desired adjustment.

U.S. Pat. No. 5,788,688 (the '688 patent) discloses a surgeon's command and control system utilizing a control panel, which duplicates the essential elements of output power settings, and configuration displays found on the control unit of each individual device. Furthermore, the control panel provides the surgeon with a video image of the entirety of the particular surgical device's control interface.

However, the system as disclosed in the '688 patent does not disclose a system capable of automatically recognizing, incorporating and downloading interfaces of the surgical devices supplied by various manufacturers into a readily usable configuration having a video display of the control interfaces for the various devices.

It is, therefore, an object of the invention to provide a communication system capable of automatically recognizing and connecting various surgical devices.

It is a further object of the invention to provide a communication system including a touchscreen that is capable of displaying replicas of control interfaces of a variety of third party and first party surgical devices.

It is yet another object of the invention to provide a communication system allowing the surgeon to remotely control first and third party devices employed in the surgery by manipulating functional areas of the replica control interfaces displayed on a touchscreen.

It is still another object of the invention to provide a communication system allowing the surgeon to provide a visual configuration of a network of first and third party devices on a touchscreen for a given surgery.

It is yet another object of the invention to provide a communication system allowing the surgeon to select familiar surgical devices, having replicas of these devices displayed on a touchscreen.

It is still another object of the invention to provide a communication system capable of updating a storage device that contains protocols associated with third party devices and replicas of control interfaces of these devices.

It is yet another object of the invention to provide a communication system that will automatically access and download control interfaces for surgical devices supplied by various manufacturers.

SUMMARY OF THE INVENTION

Accordingly, a communication system is provided that allows a surgeon to have direct command and control over various remotely located medical devices during an endoscopic surgery. Devices not specifically designed to operate with the communication system will be referred to herein as third party devices, whereas devices specifically designed to operate with the communication system will be referred to herein as, first party devices.

A universal communication system is adapted to seamlessly incorporate multiple endoscopic instruments into a network including first party and third party devices. Furthermore, the communication system is capable of connecting third party devices to the network and displaying replicas of their control interfaces on a touchscreen, which is located within the sterile environment and the surgeon's reach during the actual course of the procedure. Therefore, a surgeon is able to control the interconnected devices by adjusting functional areas of the replica control interfaces displayed on the touchscreen.

The control interface of the interconnected device may comprise but is not limited to, for instance; a replica faceplate, or a display with a pointing device, or any other interactive means by which the device may be controlled.

To provide instant recognition of third party devices on the touchscreen, the communication system has a plurality of interface devices capable of interpreting and conveying information through the bus between the touchscreen, master equipment device and a variety of slave equipment devices. Specifically, the surgeon is given an opportunity to manipulate each of the equipment devices including both first party and third party devices from the touchscreen.

Also, the communication system is capable of periodically updating its database of both first and third party devices. Preferably, the system uses an Internet communication link allowing technical personnel to visit web sites of manufacturers to scan and store necessary information allowing the latest products to be readily incorporated in the communication system.

In one advantageous embodiment, a medical communication and control system is provided comprising: a touchscreen; a controller for the touchscreen, having a controller command protocol; a first remotely controllable surgical device, having a first command protocol, controllable by said touchscreen; a second remotely controllable surgical device, having a second command protocol, controllable by said touchscreen; an interface, connected between the touchscreen controller and the first remotely controllable surgical device and the second remotely controllable surgical device, for converting the controller command protocol to the first and second command protocols, and for transforming inputs received by the touchscreen into commands for controlling the first and second remotely controllable surgical devices; and an image, replicating a control interface particular to the first and second remotely controllable surgical devices, for display on the touchscreen to receive inputs and to display a status of the first and second remotely controllable surgical devices.

In another advantageous embodiment, a medical communication and control system is provided comprising: a touchscreen; a controller for the touchscreen; a controller command protocol for the touchscreen controller; a first and a second remotely controllable surgical device; a first and a second command protocol for control of a first and a second surgical device respectively; an interface, connected between the touchscreen controller and the remotely controllable surgical devices, for converting the controller command protocol to the first and second command protocols for transforming inputs received by the touchscreen into commands for controlling the first and second remotely controllable surgical devices; and an image, replicating control interfaces particular to the remotely controllable surgical devices for display on the touchscreen to receive inputs and to display a status of the remotely controllable surgical devices.

In still another advantageous embodiment, a medical communication and control system is provided comprising: a touchscreen; a controller for the touchscreen, having a controller command protocol; a first remotely controllable surgical device, having a first command protocol, controllable by said touchscreen; a second remotely controllable surgical device, having a second command protocol, controllable by said touchscreen; and an interface, connected between the touchscreen controller and the first remotely controllable surgical device and the second remotely controllable surgical device, for converting the controller command protocol to the first and second command protocols, and for transforming inputs received by the touchscreen into commands for controlling the first and second remotely controllable surgical devices.

In yet another advantageous embodiment, a method for operating a medical communication system is provided comprising the steps of: providing a touchscreen; providing a controller for the touchscreen, having a controller command protocol; providing a first remotely controllable surgical device, having a first command protocol; providing a second remotely controllable surgical device, having a second command protocol; providing an interface, connecting the touchscreen controller to the first and second remotely controllable surgical devices; providing an image replicating the control interface of the first and second remotely controllable surgical devices for display on the touchscreen and for receiving input commands; inputting commands to the touchscreen controller for controlling the first and second remotely controllable surgical devices respectively; converting the commands from the controller command protocol to the first and second command protocols respectively; and transmitting the converted commands to the first and second remotely controllable surgical devices respectively.

In still another advantageous embodiment, a method for operating a medical communication system comprising the steps of: providing a touchscreen; providing a controller for the touchscreen; providing a controller command protocol for the touchscreen controller; providing a first remotely controllable surgical device, having a first command protocol; providing a second remotely controllable surgical device, having a second command protocol; providing an interface, connected between the touchscreen controller and the first remotely controllable surgical device and the second remotely controllable surgical device; inputting commands to the touchscreen for controlling the first remotely controllable surgical device and the second remotely controllable surgical device; converting the commands from the controller command protocol to the first and second command protocols respectively; and transmitting the converted commands to the first remotely controllable surgical device and the second remotely controllable surgical device respectively.

In yet another advantageous embodiment, a medical communication and control system is provided comprising: a remotely controllable surgical device having a control interface which is particular to said remotely controllable surgical device; a touchscreen for displaying the control interface; a controller for controlling said remotely controllable surgical device; a database, accessible by said controller; and an image, stored on said database, replicating the control interface particular to said remotely controllable surgical device; wherein said controller upon connection of said remotely controllable surgical device queries said database for said image replicating the control interface particular to said remotely controllable surgical device for display on the touchscreen to receive inputs and to display a status of the remotely controllable surgical device, and wherein if said controller does not locate said image on said database, said controller automatically downloads and stores said image on said database for use with said touchscreen.

In still another advantageous embodiment, a medical communication and control system is provided comprising: a remotely controllable surgical device having a control interface which is particular to said remotely controllable surgical device; a touchscreen for displaying the control interface; a controller for controlling said remotely controllable surgical device; a database, accessible by said controller; and an image, stored on said database, replicating the particular control interface for said remotely controllable surgical device, and for display on the touchscreen to receive inputs and to display a status of the remotely controllable surgical device; wherein said controller upon connection of said remotely controllable surgical device queries said database for said image replicating the control interface particular to said remotely controllable surgical device for display on the touchscreen to receive inputs and to display a status of the remotely controllable surgical device, and wherein said controller periodically queries, downloads and saves updated images particular to various remotely controllable surgical devices to said database.

The invention and its particular features and advantages will become more apparent from the following detailed description considered with reference to the accompanying drawings.

BRIEF DESCRIPTION OF THE DRAWINGS

FIGS. 5A–5D show a sequence of steps for preparing for and performing an endoscopic surgery by utilizing a touchscreen in accordance with one advantageous embodiment of the communication system.

DETAILED DESCRIPTION OF THE DRAWINGS

Figure 1:
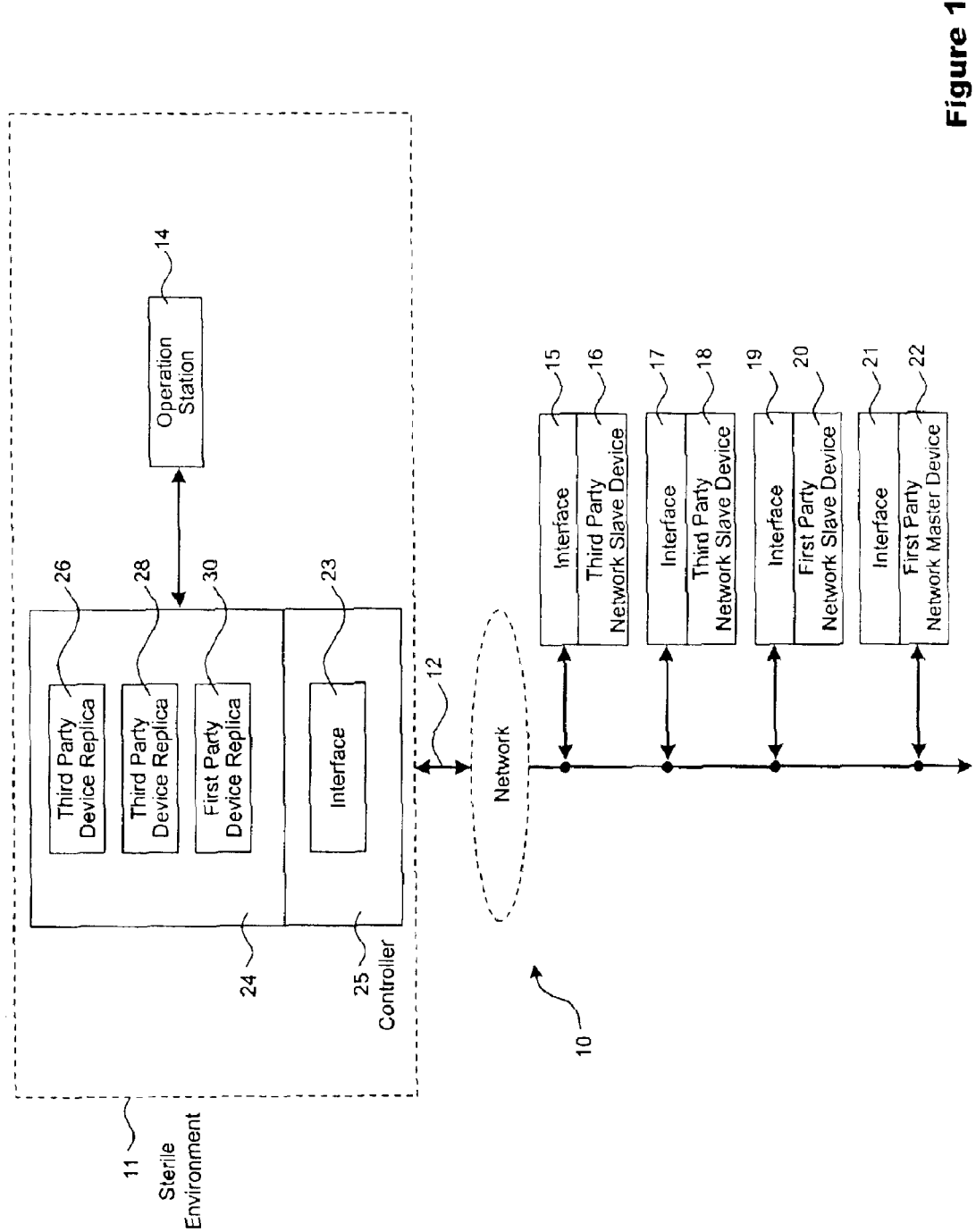
FIG. 1 is a block diagram of the communication system.

A universal communication system 10, as shown in FIG. 1, is formed of a bus 12 coupled to a variety of different medical slave devices 16, 18 and 20 and at least one master medical device 22. A touchscreen 24, which displays remote control access for various surgical devices during the operation, is located within the sterile environment 11 and within reach of the surgeon performing the procedure at the operation station 14. Particularly, the surgeon is able to manipulate the course of the operation by connecting the medical devices to and disconnecting them from the bus 12 by touching the screen 24.

As explained in the aforementioned patent applications Ser. No. 09/180,692 and Ser. No. 09/411,412, communication with and control over various surgical devices can be implemented using hardware and software elements. Thus, each of the devices shown in FIG. 1 has a respective interface 15, 17, 19, 21 and software to provide communication between the slave and master medical devices through the bus 12. In addition, the touchscreen 24 is also provided with an interface device 23 capable of communicating with the devices through the bus 12. The communication system uses a modified CAN bus system which interconnects, either by means of a cable or wireless communication, with the other medical devices that are a part of the system 10. The interface devices are typically, for instance, electronic devices containing microprocessors.

A variety of medical devices utilized in surgical procedures can include multiple third party devices such as 16 and 18 in addition to various other surgical devices such as first party device 20 and master device 22. FIG. 1 depicts two third party slave devices, one first party slave device and one master device. However, any combination of third party and first party slave devices can be utilized along with a master device. The interface of each device is designed to understand the differing incoming signal commands, interpret and then respond to them in accordance with certain protocols specific to the communication system. In other words, each interface provides compatibility between the bus system 12 and each of the connected devices, regardless whether or not the various surgical devices, such as third party devices 14 and 16 or first party device 20 and master device 22, are originally designed to operate with the bus 12.

As shown in FIG. 1, the device 22 serves as a network master that may control the other connected surgical devices. Alternatively, control of the other surgical devices may be accomplished by any other master capable device connected. One of the control functions of the master device 22 includes sorting out and directing the signals, which are generated by the touchscreen 24 in response to commands issued by the surgeon, to all the various connected surgical devices utilized in the procedure. The touchscreen 24 is connected to controller 25, which also has an interface 23 coupled to the bus 12.

The touchscreen 24 is capable of displaying exact replicas 26 and 28 of device control interfaces supplied by various manufacturers, which may be familiar to the surgeon based on his prior experience. The touchscreen 24 is also capable of displaying an exact replica 30 of a device control interface that is supplied by the touchscreen 24 system manufacturer. This will allow the surgeon to utilize familiar equipment during the procedure, allowing the surgeon to adjust these devices during the surgery directly from the operation station.

Accordingly, the surgeon need only touch the replica control interface appearing on the touchscreen 24 to generate a signal that is conveyed to controller 25 and through the interface 23 to the bus 12 and master device 22 to operate the respective slave device. Since the surgeon is familiar with the layout of the control interfaces, he does not need time to learn and become familiar with unknown devices.

Although the above-described system relates to manipulation of the devices during the surgery, the system can also be utilized during the pre-surgical stage when an operator configures the network including a variety of devices located in remote locations and connected to the network. Since many parameters of the endoscopic devices are standard, these devices can be set before the actual operation begins. Furthermore, the touchscreen 24 can allow an operator to configure and control several networks at once, which may be particularly convenient for a communication system interconnecting satellite medical locations to a central hospital. Finally, subject to laws and regulations governing a given geographical area, endoscopic operations may be performed utilizing the above-described system via a network connection, which may comprise, for instance, an Intranetwork connection and/or an Internet connection, shown in phantom lines in FIG. 1.

Figure 2:
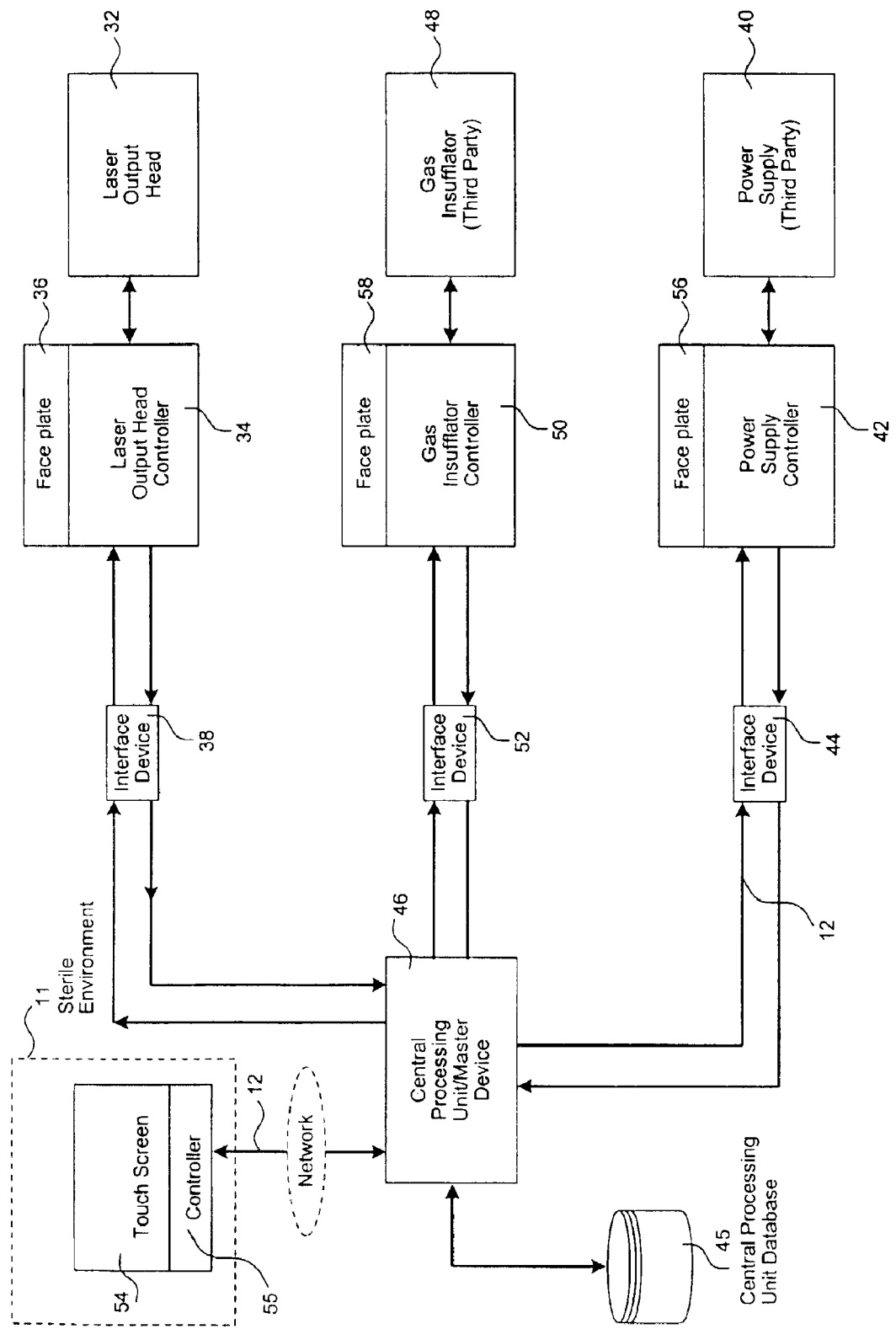
FIG. 2 is a block diagram of the communication system.

FIG. 2 illustrates an application of the system 10 to a laser arthroscopic surgery. Generally, a laser output head 32, having a laser output head controller 34 with a control interface 36, are utilized in this type of surgery. The laser output head 32 is powered by a power supply 40, which may be manufactured for example, by a third party. The power supply 40 is controlled by a power supply controller 42 with a control interface 56, capable of controlling the duration and number of pulses. To distend an anatomical area to be operated upon, the network further includes a gas insufflator 48 controlled by a gas insufflator controller 50 with a control interface 58, which provides regulation of the inlet pressure. The devices 32, 40 and 48, which are slave devices, have interface devices 38, 44 and 52, respectively, capable of communicating with a central processing unit or master device 46 (such as a computer). A central processing unit database 45 is accessible by the central processing unit 46. Video touchscreen 54 and controller 55 located in the sterile environment of the operation station 11 complete the network, and the touchscreen 54 displays control interfaces particular to each of the control devices.

Control interfaces particular to each of the control devices may be stored on the central processing unit database 45. Upon connection of a control device to the central processing unit 46, the central processing unit 46 may automatically query the central processing unit database 45 for the control interface particular to that control device. If the particular control device interface is found in the central processing unit database 45, it may be automatically sent to the touchscreen 54 for display and control of the particular control device. If however, the particular control device interface is not found in the central processing unit database 45, the central processing unit 46 may automatically query a website corresponding to the particular control device so as to download the particular control device interface over the network connection. Alternatively, the central processing unit may prompt the user to load the particular control device interface. In addition, the central processing unit 46 may periodically update particular control device interfaces by connecting to websites corresponding to the particular control device. The network connection may comprise, for instance but not limited to, an Intranetwork, a Local Area Network (LAN), a Wide Area Network (WAN) or the Internet.

Figure 3:
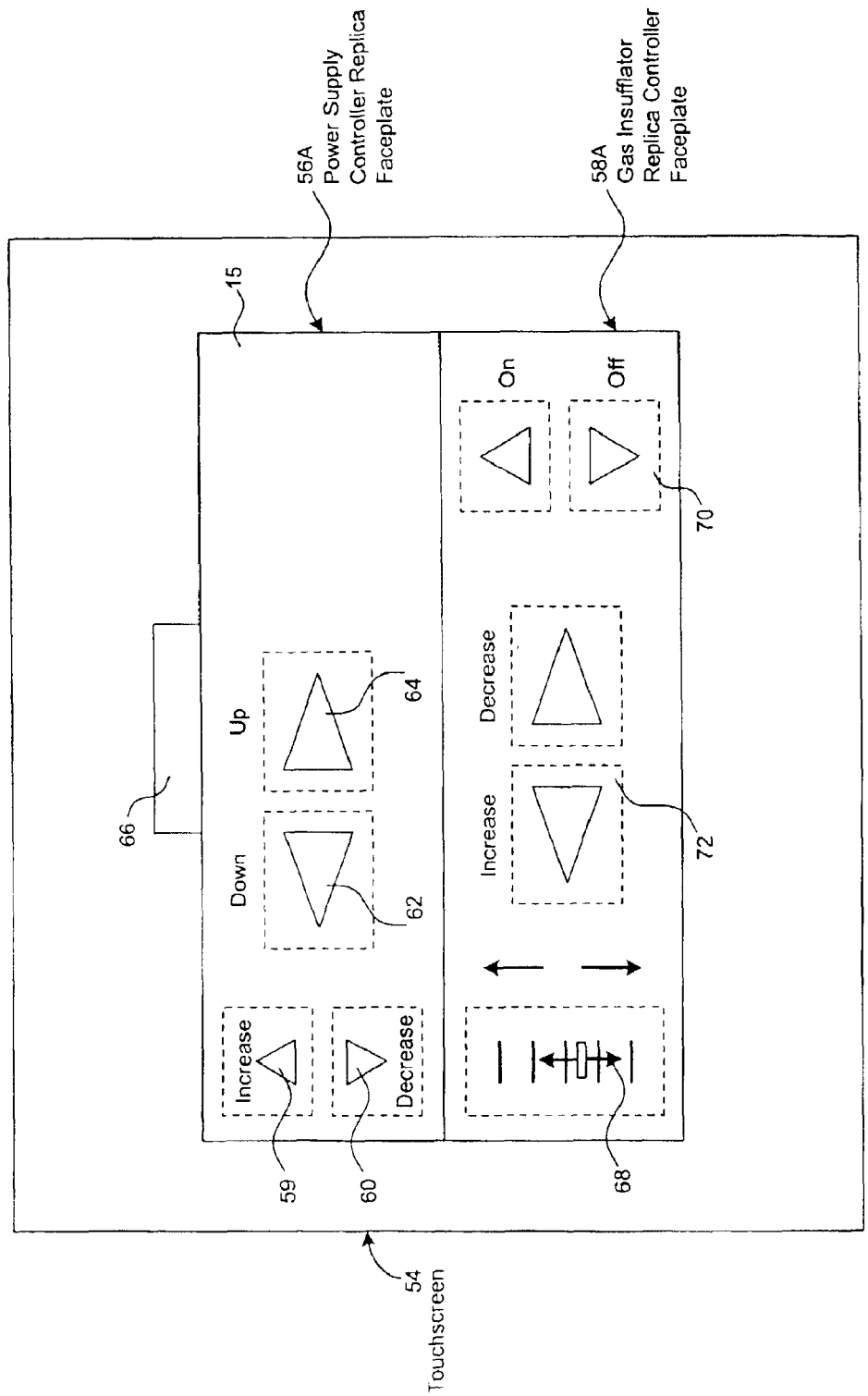
FIG. 3 is a perspective view illustrating a replica control interface displayed on a touchscreen that is utilized for surgical procedures.
Figure 4:
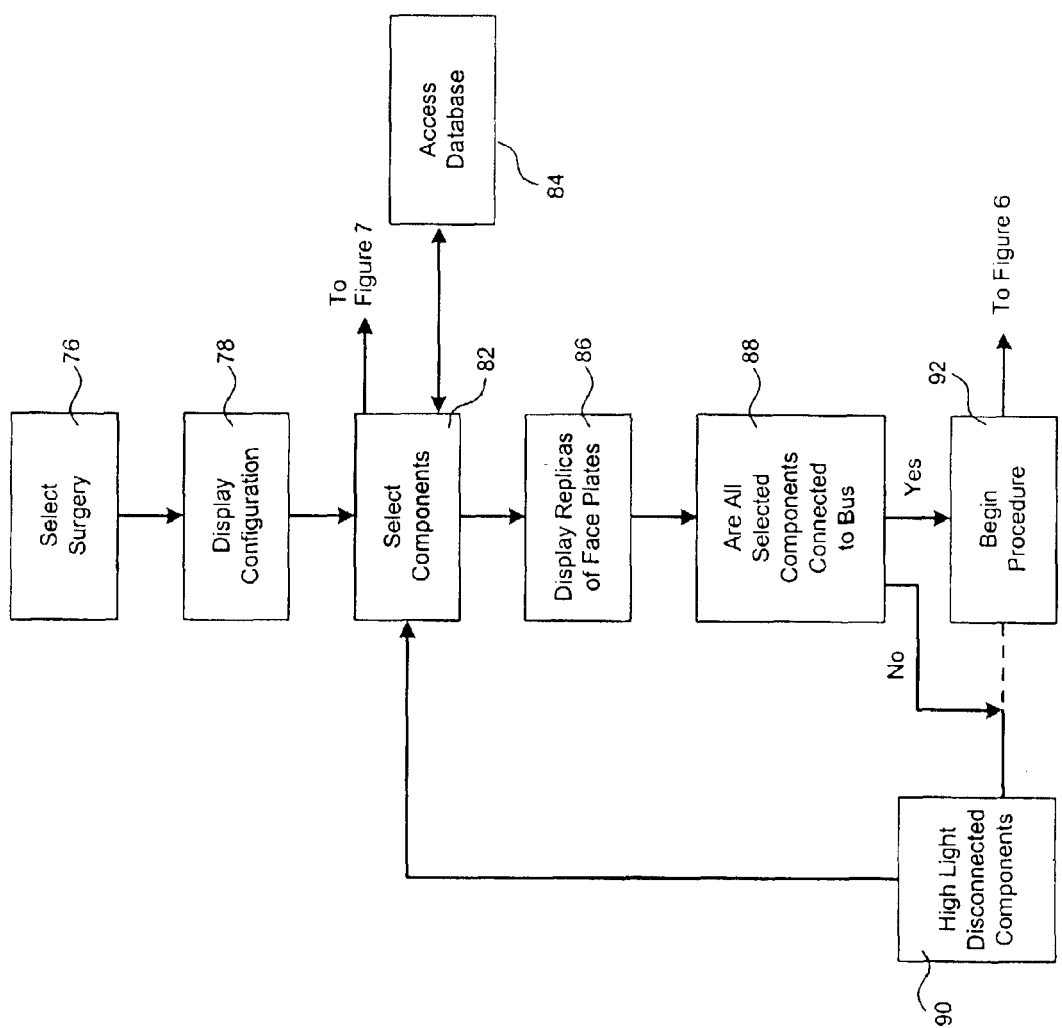
FIG. 4 is flow chart of one advantageous embodiment for operating the communication system.

Accordingly, as shown in FIG. 3, the touchscreen displays replicas of the control interfaces of three control components 36, 42 and 50 shown in FIG. 2, so the surgeon, who typically is familiar with the layout of actual control interfaces of these devices, simply manipulates a replica of the actual switch or button. A control signal generated in response to this motion regulates the corresponding control of the actual control interface to provide a change in existing parameters. The control signal is routed to the corresponding device by the controller, which in turn receives inputs from the touchscreen. The bus 12 may be formed with wires or include wireless channels.

For illustrative purposes, two replicas of control interfaces 56 and 58 of the power supply controller 42 and insufflator controller 50, respectively, are shown in FIG. 3. First, with respect to power supply replica control interface 56A, buttons 59 and 60 point in different directions to allow the surgeon to increase and decrease, respectively, the duration of beam emitted by the laser head 32. In addition, to increase or decrease the number of pulses, the surgeon has to touch functional areas 62, 64. A small visual screen 66 above these buttons will actually illustrate a numeral representing the selected number of pulses.

With respect to gas insufflator replica control interface 58A, a slider 68 replicates the actual slider controlling a flow rate at which the gas is supplied to the anatomic area to be operated on. Two oppositely pointing arrow-buttons 70 may represent an on/off switch, whereas buttons 72 replicate a pressure regulator. Each of the replicated switches and buttons can be color-coded to help the surgeon avoid accidental activation of the adjacent controls. Note, that although third party devices have been discussed, the touchscreen also can display control interface replicas of first party surgical devices.

FIGS. 4 and 5A–5D illustrate the sequence of steps for the surgeon to select and configure a desired network. The communication system is provided with electronics having software that allows the surgeon to follow the above- and below-described procedures. The surgeon looking at the touchscreen first selects a type of endoscopic operation he or she will perform at 76. A list of the surgeries is shown, for instance, in FIG. 5A, but may include many other various surgical procedures. For instance, the screen layout may illustrate the features in various screen configurations. To activate a surgery type menu, the surgeon can touch the appropriate area of the screen.

Figure 5B:
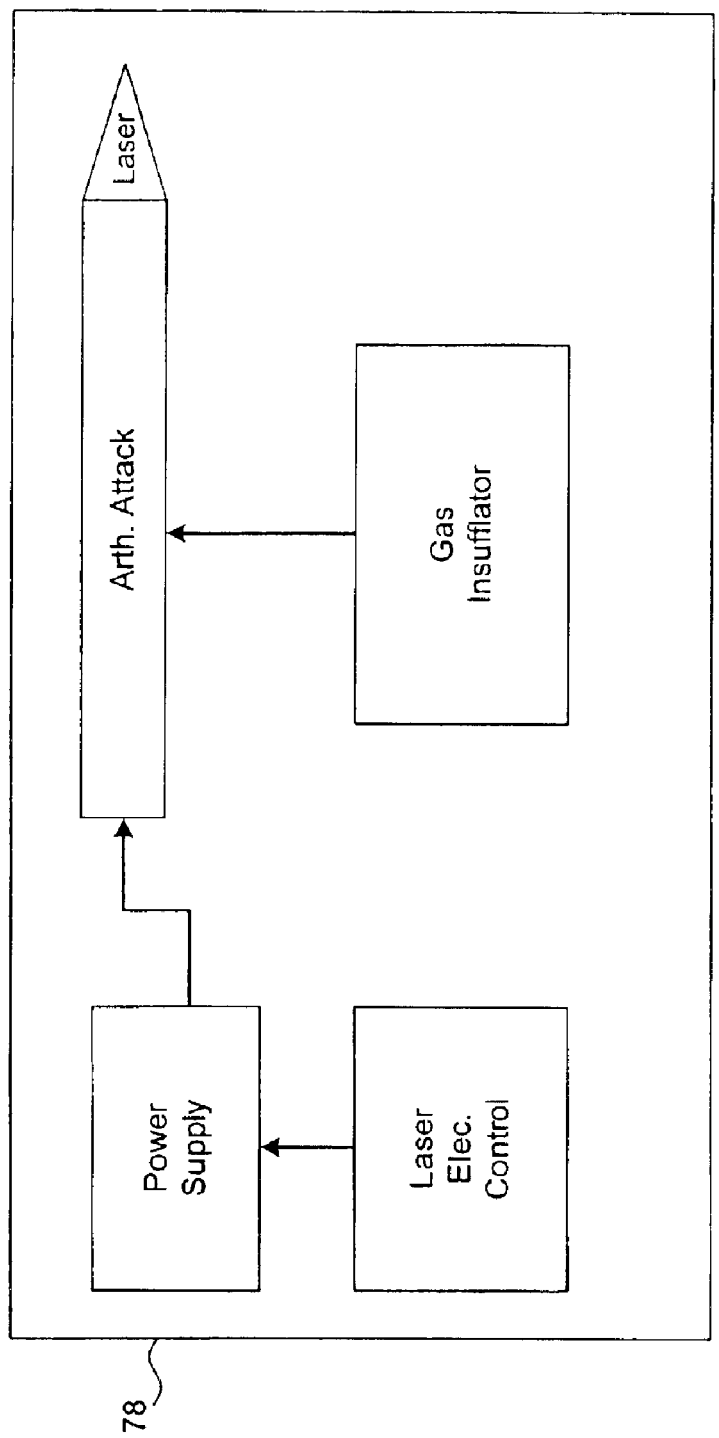

After selecting the surgery, a diagrammatic view of the selected surgery may be displayed at 78 either automatically or upon touching, for example, an area denoted as "diagram" on the screen. For instance, while the diagram or configuration illustrated in FIG. 5B shows a number of blocks representing necessary medical instruments for the selected surgery, it is possible to view actual images of the devices. Thus, FIG. 5B shows a replica of the first surgery selection in FIG. 5A and the arthroscopic surgery network described above in reference to FIGS. 2 and 3, including a laser, power supply, laser control and a gas insufflator.

Assuming that the surgeon would like to select each of the shown devices in accordance with his personal preferences, he/she then chooses a "nomenclature" menu 80 to display a matrix 81 as shown in detail in FIG. 5C. Presented with a variety of options representing different manufactures, the surgeon can select components 82 with which he/she is familiar. Accordingly, during the course of the operation, the surgeon does not need to familiarize himself with unknown control interfaces, and, as a consequence, he/she may be more efficient, and feel more comfortable working with familiar instruments. Alternatively, instead of having all four devices shown in FIG. 5B, the surgeon may choose any particular device and have a list showing available devices for only the chosen position.

Typically, a master device is provided with a database, which is either integral to or located at a distance from the master device. Upon the surgeon's selection, the master device accesses database 84 to retrieve a protocol and control interface image of a selected device.

Figure 5D:
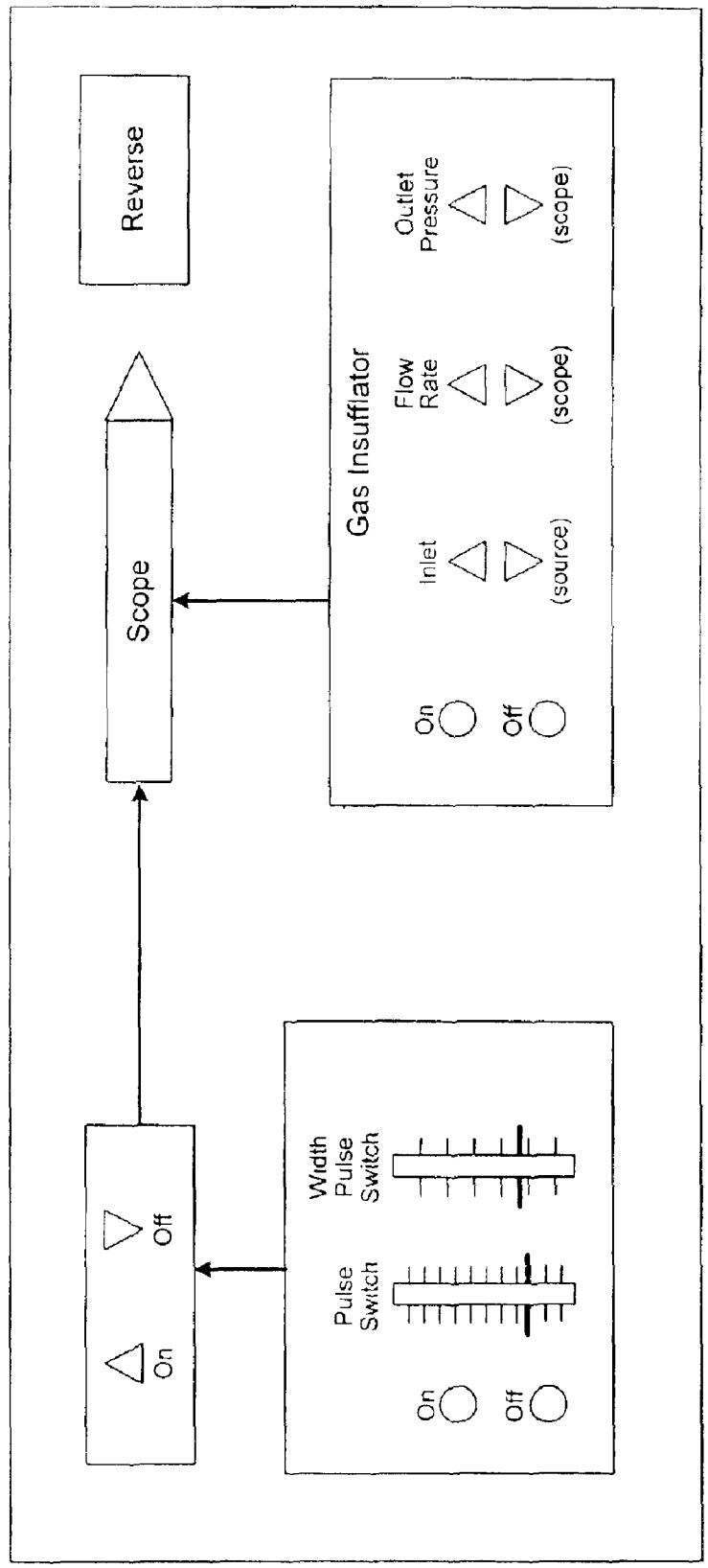

After the various devices are selected and displayed at 86, the surgeon is presented with a view, which can be similar to FIG. 3, wherein separately positioned rectangles are arranged in a row. Alternatively, as shown in FIG. 5D, the actual layout of the selected surgery is represented by the rectangles interconnected with one another to provide visual display of the actually interconnected devices.

In accordance with a safety feature of the present invention, it is foreseen to verify each of the surgeon's commands before and during the actual surgery. Software executed on the master device or touchscreen can easily be programmed to perform various operations indicating completeness of the configuration as well as completeness of a control signal from the touchscreen representing the requested command during the operation. For example, after all of the elements have been selected, their connection is verified at 88 and if some of the selected devices remain disconnected for any reason, the touchscreen will have these devices highlighted at 90. This may happen, for example, if one or several of the selected devices are not stored in the database or simply malfunction, and allows the surgeon to select a different device functionally similar to the disconnected one.

Furthermore, to provide the surgeon with an indication of the completeness of the requested command, the slave device may generate a feedback signal in response to the control signal from the touchscreen. After the master device processes the feed back signal, the touchscreen will be able to indicate that the desired operation has been completed. Thus, for example, if the real control interface of the slave device is provided with a red LED indicating that the device is on, the touchscreen will display the red light at the corresponding functional area in response to turning the device in an "on" mode. Alternatively, a verbal message including for example "ON" or "OFF" can provide the surgeon with the information as to whether the slave device has been turned on in response to the surgeon's command even if the real control interface does not have this function.

Figure 6:
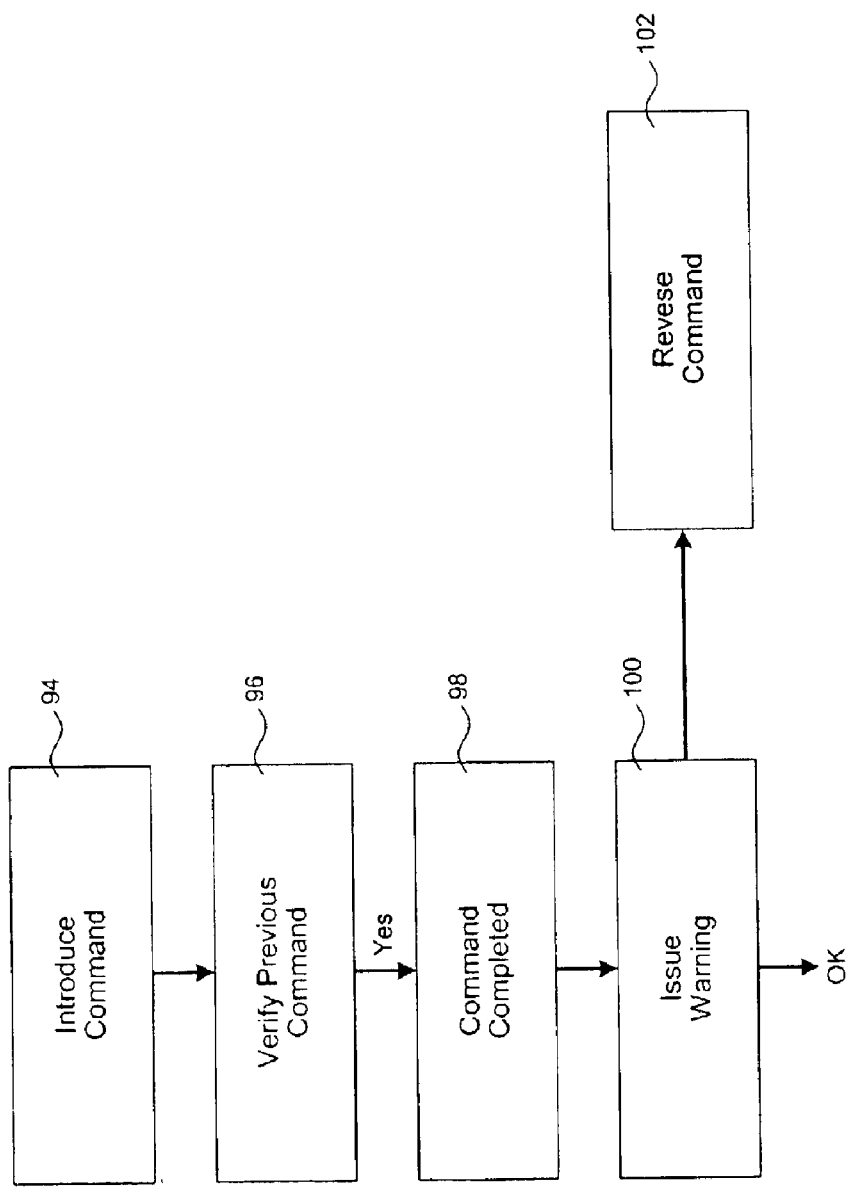
FIG. 6 is a flowchart of a surgery safety system utilized by the communication system.

During the surgery, which begins at 92, at least some of the surgeon's commands introduced at 94 of FIG. 6 should be verified at 96 to avoid unwanted actions. Thus, software executed on the master or even slave devices is capable of identifying the requested command as dangerous. For example, pressing the button "OFF" on the replica of one of the employed devices. If the requested command may lead to a dangerous result, then the touchscreen will display a request asking the surgeon to verify the previous command 96. If the command is confirmed, then the system responds to it by performing necessary connections or manipulations at 98. However, it is possible that the surgeon mistakenly confirms the undesirable command. For example, the surgeon has interrupted the gas supply during the surgery. After the command has been completed, a screen may issue a warning 100 indicating the exact location and nature of the threatening situation. If the command were intentional, the warning would be simply ignored. If, however, the command were issued and confirmed by accident, the surgeon can immediately reverse the command 102, and the system would automatically restore the situation as it has been before the command was issued.

Figure 7:
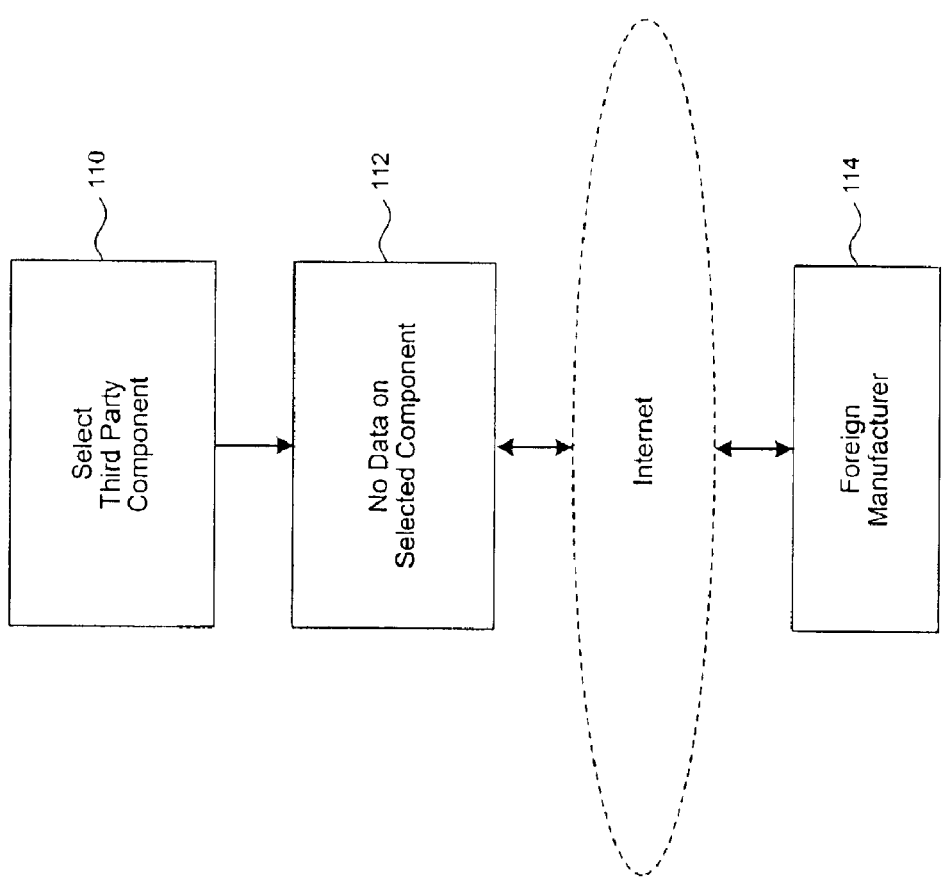
FIG. 7 is a diagrammatic view illustrating an advantageous embodiment of the communication system communicating with various surgical devices.

As endoscopic surgery becomes widely used for a variety of medical procedures, manufacturing of medical endoscopic devices rapidly diversifies. To keep the database fully functional, it should be periodically updated. One of the most efficient ways of keeping the information up to date is to gather it from a variety of manufacturers typically placing necessary real views and protocols of the newly manufactured devices on their web sites, as shown in FIG. 7. The surgeon selects the third party component 110. If the system 10 does not have the necessary data on the selected component 112 to operate it correctly, the system may automatically access the manufacturer 114 to obtain the necessary information via an Internet connection. It is also possible that the query for information by the system 10 can be initiated and performed by a request from the surgeon.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A medical communication and control system comprising:
   a touchscreen;
   a controller for the touchscreen, having a controller command protocol;
   a first remotely controllable surgical device, having a first command protocol, controllable by said touchscreen;
   a second remotely controllable surgical device, having a second command protocol, controllable by said touchscreen;
   an interface, connected between the touchscreen controller and the first remotely controllable surgical device and the second remotely controllable surgical device, for converting the controller command protocol to the first and second command protocols, and for transforming inputs received by the touchscreen into commands for controlling the first and second remotely controllable surgical devices; and
   an image, replicating a control interface particular to the first and second remotely controllable surgical devices, for display on the touchscreen to receive inputs and to display a status of the first and second remotely controllable surgical devices.

2. The medical communication system of claim 1 wherein the interface comprises a microprocessor.

3. The medical communication system of claim 1 wherein at least one remotely controllable surgical device has an electronic master capability and at least one other remotely controllable surgical device is a slave.

4. The medical communication system of claim 3 further comprising software, executing on the at least one remotely controllable surgical device with master capability for routing control signals to the at least one remotely controllable surgical device that is a slave.

5. The medical communication system of claim 3 further comprising software, executing on the at least one remotely controllable surgical device with master capability, for receiving a feedback signal from the at least one remotely controllable surgical device that is a slave.

6. The medical communication system of claim 1 further comprising software, executing on the interface device, for displaying a scroll down menu of a variety of surgical procedures.

7. The communication system of claim 3 further comprising a database accessible by the controller for storing the replica control interfaces of various surgical devices.

8. The medical communication system of claim 7 further comprising software, executing on the interface device for querying the database.

9. The medical communication system of claim 7 further comprising software, executing on the device with master capability, for querying sources of information through a network connection, to update the database.

10. The medical communication system of claim 9 wherein the network connection comprises the Internet.

11. The medical communication system of claim 1 further comprising software executing on the interface device, for verifying the outputs.

12. The medical communication system of claim 11 further comprising software executing on the interface device for reversing the outputs after the outputs have been verified.

13. A medical communication and control system comprising:
   a touchscreen;
   a controller for the touchscreen;
   a controller command protocol for the touchscreen controller;

a first and a second remotely controllable surgical device;

a first and a second command protocol for control of a first and a second surgical device respectively;

an interface, connected between the touchscreen controller and the remotely controllable surgical devices, for converting the controller command protocol to the first and second command protocols for transforming inputs received by the touchscreen into commands for controlling the first and second remotely controllable surgical devices; and an image, replicating control interfaces particular to the remotely controllable surgical devices for display on the touchscreen to receive inputs and to display a status of the remotely controllable surgical devices.

14. The medical communication system of claim 13 wherein the interface comprises a microprocessor.

15. The medical communication system of claim 13 wherein at least one remotely controllable surgical device has an electronic master capability and at least one other remotely controllable surgical device is a slave.

16. The medical communication system of claim 15 further comprising software, executing on the at least one remotely controllable surgical device with master capability for routing control signals to the at least one remotely controllable surgical device that is a slave.

17. The medical communication system of claim 15 further comprising software, executing on the at least one remotely controllable surgical device with master capability, for receiving a feedback signal from the at least one remotely controllable surgical device that is a slave.

18. A medical communication and control system comprising:

a touchscreen;

a controller for the touchscreen, having a controller command protocol;

a first remotely controllable surgical device, having a first command protocol, controllable by said touchscreen;

a second remotely controllable surgical device, having a second command protocol, controllable by said touchscreen; and an interface, connected between the touchscreen controller and the first remotely controllable surgical device and the second remotely controllable surgical device, for converting the controller command protocol to the first and second command protocols, and for transforming inputs received by the touchscreen into commands for controlling the first and second remotely controllable surgical devices;

wherein said first remotely controllable surgical is a first party device and said second remotely controllable surgical device is a third party device, the second command protocol being different from the first command protocol.

19. The medical communication system of claim 18 wherein the interface comprises a microprocessor.

20. The medical communication system of claim 18 wherein at least one remotely controllable surgical device has an electronic master capability and at least one other remotely controllable surgical device is a slave.

21. The medical communication system of claim 20 further comprising software, executing on the at least one remotely controllable surgical device with master capability for routing control signals to the at least one remotely controllable surgical device that is a slave.

22. The medical communication system of claim 20 further comprising software, executing on the at least one remotely controllable surgical device with master capability, for receiving a feedback signal from the at least one remotely controllable surgical device that is a slave.

23. A method for operating a medical communication system comprising the steps of:

providing a touchscreen;

providing a controller for the touchscreen, having a controller command protocol;

providing a first remotely controllable surgical device, having a first command protocol;

providing a second remotely controllable surgical device, having a second command protocol;

providing an interface, connecting the touchscreen controller to the first and second remotely controllable surgical devices;

providing an image replicating the control interface of the first and second remotely controllable surgical devices for display on the touchscreen and for receiving input commands;

inputting commands to the touchscreen controller for controlling the first and second remotely controllable surgical devices respectively;

converting the commands from the controller command protocol to the first and second command protocols respectively; and transmitting the converted commands to the first and second remotely controllable surgical devices respectively.

24. The method of claim 23 further comprising the step of providing at least one remotely controllable surgical device with electronic master capability and providing at least one other remotely controllable surgical device as a slave.

25. The method of claim 24 further comprising the step of providing software, executing on the at least one remotely controllable surgical device with master capability for routing control signals to the at least one remotely controllable surgical device that is a slave.

26. The method of claim 24 further comprising the step of providing software, executing on the at least one remotely controllable surgical device with master capability, for receiving a feedback signal from the at least one remotely controllable surgical device that is a slave.

27. A method for operating a medical communication system comprising the steps of:

providing a touchscreen;

providing a controller for the touchscreen;

providing a controller command protocol for the touchacreen controller;

providing a first remotely controllable surgical device, having a first command protocol;

providing a second remotely controllable surgical device, having a second command protocol;

providing an interface, connected between the touchscreen controller and the first remotely controllable surgical device and the second remotely controllable surgical device;

inputting commands to the touchscreen for controlling the first remotely controllable surgical device and the second remotely controllable surgical device;

converting the commands from the controller command protocol to the first and second command protocols respectively; and transmitting the converted commands to the first remotely controllable surgical device and the second remotely controllable surgical device respectively;

wherein said first remotely controllable surgical is a first party device and said second remotely controllable surgical device is a third party device, the second command protocol being different from the first command protocol.

28. A medical communication and control system comprising:
a remotely controllable surgical device having a control interface which is particular to said remotely controllable surgical device;
a touchscreen for displaying the control interface;
a controller for controlling said remotely controllable surgical device;
a database, accessible by said controller; and
an image, stored on said database, replicating the control interface particular to said remotely controllable surgical device;
wherein said controller upon connection of said remotely controllable surgical device queries said database for said image replicating the control interface particular to said remotely controllable surgical device for display on the touchscreen to receive inputs and to display a status of the remotely controllable surgical device, and wherein if said controller does not locate said image on said database, said controller automatically downloads and stores said image on said database for use with said touchscreen.

29. The medical communication and control system of claim 28 wherein said controller is connected to a network and the automatic downloading takes place over the network.

30. The medical communication and control system of claim 28 wherein said controller periodically queries, downloads and saves updated images particular to various remotely controllable surgical devices on said database.

31. The medical communication and control system of claim 29 wherein the network comprises the Internet.

32. The medical communication and control system of claim 29 wherein the network comprises an Intranet.

33. A medical communication and control system comprising:
a remotely controllable surgical device having a control interface which is particular to said remotely controllable surgical device;
a touchscreen for displaying the control interface;
a controller for controlling said remotely controllable surgical device;
a database, accessible by said controller; and
an image, stored on said database, replicating the particular control interface for said remotely controllable surgical device, and for display on the touchscreen to receive inputs and to display a status of the remotely controllable surgical device;
wherein said controller upon connection of said remotely controllable surgical device queries said database for said image replicating the control interface particular to said remotely controllable surgical device for display on the touchscreen to receive inputs and to display a status of the remotely controllable surgical device, and wherein said controller periodically queries, downloads and saves updated images particular to various remotely controllable surgical devices to said database.

34. The medical communication and control system of claim 33 wherein said controller is connected to a network and the periodic querying, downloading and saving takes place over the network.

35. The medical communication and control system of claim 33 wherein said controller automatically downloads said image replicating the control interface particular to said remotely controllable surgical device and stores said image on said database for use with said touchscreen.

36. The medical communication and control system of claim 34 wherein the network comprises the Internet.

37. The medical communication and control system of claim 34 wherein the network comprises an Intranet.

* * * * *